(12) United States Patent
Georgi et al.

(10) Patent No.: US 9,179,885 B2
(45) Date of Patent: Nov. 10, 2015

(54) INTEGRATED WORK-FLOW FOR ACCURATE INPUT FUNCTION ESTIMATION

(75) Inventors: Jens-Christoph Georgi, Aachen (DE); Manoj Narayanan, Snohomish, WA (US)

(73) Assignee: Koninklijke Philips N.V., Eindhoven (NL)

( * ) Notice: Subject to any disclaimer, the term of this patent is extended or adjusted under 35 U.S.C. 154(b) by 203 days.

(21) Appl. No.: 13/993,091

(22) PCT Filed: Dec. 14, 2011

(86) PCT No.: PCT/IB2011/055662
§ 371 (c)(1),
(2), (4) Date: Jun. 11, 2013

(87) PCT Pub. No.: WO2012/080960
PCT Pub. Date: Jun. 21, 2012

(65) Prior Publication Data
US 2013/0261440 A1 Oct. 3, 2013

Related U.S. Application Data

(60) Provisional application No. 61/422,698, filed on Dec. 14, 2010.

(51) Int. Cl.
*A61B 6/00* (2006.01)
*A61B 6/03* (2006.01)
*G01T 1/16* (2006.01)

(52) U.S. Cl.
CPC ............... *A61B 6/583* (2013.01); *A61B 6/032* (2013.01); *A61B 6/037* (2013.01); *A61B 6/4417* (2013.01); *A61B 6/461* (2013.01); *A61B 6/486* (2013.01); *A61B 6/503* (2013.01); *A61B 6/504* (2013.01); *A61B 6/507* (2013.01); *A61B 6/54* (2013.01); *G01T 1/16* (2013.01)

(58) Field of Classification Search
CPC ....... A61B 6/032; A61B 6/037; A61B 6/4417; A61B 6/461; A61B 6/486; A61B 6/503; A61B 6/504; A61B 6/507; A61B 6/54; A61B 6/583; G01T 1/16
See application file for complete search history.

(56) References Cited

U.S. PATENT DOCUMENTS

| | | |
|---|---|---|
| 2007/0299335 A1 | 12/2007 | Declerck et al. |
| 2008/0183447 A1 | 7/2008 | Fischer et al. |
| 2009/0018438 A1 | 1/2009 | Schroder et al. |

OTHER PUBLICATIONS

Boellaard, R., et al.; FDG PET and PET/CT: EANM procedure guidelines for tumour PET imaging: version 1.0; 2010; Eur. J. Nucl. Med. Mol. Imaging; 37:181-200.

(Continued)

*Primary Examiner* — Michael Rozanski

(57) ABSTRACT

When estimating an arterial input function or a patient under study, cross-calibration factors are generated by comparing nuclear scan data of a radioactive material (e.g., F18) and measuring a sample of the radioactive material in a gamma counter. The derived cross-calibration factors are applied to venous samples collected from the patient during a nuclear scan after infusion with a radioactive tracer, to convert gamma values counted by the gamma counter into concentration values. The concentration values are used to optimize an initial estimated input function, thereby generating an arterialized input function.

19 Claims, 4 Drawing Sheets

(56) References Cited

OTHER PUBLICATIONS

Chen, K., et al.; Characterization of the image-derived carotid artery input function using independent component analysis for the quantitation of [18F] fluorodeoxyglucose positron emission tomography images; 2007; Phys. Med. Biol.; 52:7055-7071.

Dimitrakopoulou-Strauss, A., et al.; Prognostic Aspects of 18F-FDG PET Kinetics in Patients with Metastatic Colorectal Carcinoma Receiving FOLFOX Chemotherapy; 2004; The Journal of Nuclear Medicine; 45(9)1480-1487.

Hoekstra, C. J., et al.; On the use of image-derived input functions in oncological fluorine-18 fluorodeoxyglucose positron emission tomography studies; 1999; European Journal of Nuclear Medicine; 26(11)1489-1492.

Mankoff, D. A., et al.; Quantitative Analysis in Nuclear Oncologic Imaging; 2006; Quantitative Analysis in Nuclear Medicine Imaging; Springer; pp. 494-536.

O'Sullivan, F., et al.; Kinetic Quantitation of Cerebral PET-FDG Studies Without Concurrent Blood Sampling: Statistical Recovery of the Arterial Input Function; 2010; IEEE Trans. on Medical Imaging; 29(3)610-624.

Spinelli, A. E., et al.; Pixel-based Partial Volume Correction of small animal Pet images using Point Spread Function system characterization: evaluation of effects on cardiac output, perfusion and metabolic rate using parametric images; 2008; IEEE Nuclear Science Symposium Conference Record; M06-395:4260-4265.

Tseng, J., et al.; 18F-FDG Kinetics in Locally Advanced Breast Cancer: Correlation with Tumor Blood Flow and Changes in Response to Neoadjuvant Chemotherapy; 2004; J. Nucl. Med.; 45:1829-1837.

INTEGRATED WORK-FLOW FOR ACCURATE INPUT FUNCTION ESTIMATION

CROSS REFERENCE TO RELATED APPLICATIONS

This application is a national filing of PCT application Serial No. PCT/IB2011/055662, filed Dec. 14, 2011, published as WO 2012/080960 A2 on Jun. 21, 2012, which claims the benefit of U.S. provisional application Ser. No. 61/422,698 filed Dec. 14, 2010, which is incorporated herein by reference.

The present application finds particular application in positron emission tomography (PET) systems, particularly involving arterial input function estimation. However, it will be appreciated that the described technique may also find application in other medical input function estimation systems, other patient modeling scenarios, or other input function estimation techniques.

Continued improvements in the hardware capabilities of current generation medical imaging scanners have generated increased interest in quantitative imaging. Accurate determination of changes in physiological parameters during or at the completion of therapy is important in determining the effectiveness of treatment. For example, PET imaging incorporating pharmacokinetic modeling can provide absolute quantification measures of metabolism, perfusion, and proliferation among others. Monitoring changes in many of these parameters could lead to more personalized treatment strategies, whereby ineffective therapies could be altered or discontinued early on and alternative treatments offered. If pharmacokinetic modeling techniques are employed for absolute quantitative measurements, an accurately measured input function is important.

While qualitative (visual) impressions of PET uptake are useful in identifying/detecting the presence of cancer or other conditions, there is a clear need in the art for accurate and reproducible quantification of the uptake of an injected pharmacological tracer, e.g. fluorodeoxyglucose (FDG), at suspected sites, during the course of treatment to evaluate treatment effectiveness. This can be done by measuring relative changes in the tracer uptake over time and correlating this to other measures of clinical response.

In PET imaging, the current clinical paradigm towards a more objective uptake measure is to use the semi-quantitative standard-uptake value (SUV) taken at a given point in time after tracer injection (typically 50-60 min post-injection). The SUV measure, while easy to use clinically, is affected by a large number of factors including, time of acquisition, lack of specificity between metabolized and un-metabolized tracer, as well as variable blood pool clearance. Dynamic imaging initiated at the time of tracer injection, in combination with modeling of the acquired time-activity-curves (TAC), i.e. the underlying pharmacokinetics, provides the ability to make quantitative measurements of processes such as metabolism, hypoxia, proliferation and perfusion. There is growing evidence that kinetic analysis may be superior to standard techniques in evaluating treatment response.

As mentioned previously, accurate quantification depends strongly on the quality of the measured blood (plasma) input function. One approach is to acquire a number of arterial blood samples (i.e., an arterial input function) during the dynamic study. However, this procedure is not used routinely due to patient safety considerations. Moreover, getting institutional review board (IRB) approvals for clinical studies including arterial blood sampling can be very challenging.

An alternate approach is to use image-derived input functions by placing regions-of interest (ROIs) in the blood pool (e.g. left ventricle, aorta). However, considerations such as limited scanner resolution and sub-optimal temporal sampling of the resultant TAC will affect the quality of the image-derived input functions as explained below.

Thus, in nuclear imaging, it is desirable to derive a quantitative measure of the underlying physiological processes such as metabolism or proliferation. This can be achieved by using kinetic modeling techniques which requires an accurately measured blood input function. After administration of a radioactive tracer to a subject, the bolus of activity usually peaks within the first minute and rapidly decreases and levels off to a background level over time. This input function can be measured by collecting a plurality of arterial blood samples at short time intervals during the early part of the scan, followed by sparsely sampled measurements for the remainder of the scan. However, arterial blood sampling is not good clinical practice due to safety and patient comfort considerations. Instead, it is customary to generate an image focused on arterial blood to use as a reference. However, this approach has two drawbacks. First, due to limited scanner resolution, pixels depicting the arterial blood tend to be inaccurate, sampling not just the blood but also surrounding tissue. Second, the coarse temporal sampling will reduce the apparent peak amplitude of the input function, resulting in incorrect kinetic model estimates.

The present application provides new and improved systems and methods for optimizing an input function during a nuclear scan, which overcome the above-referenced problems and others.

In accordance with one aspect, a system that facilitates cross-calibrating a nuclear scanner to a gamma counter includes a nuclear scanner that scans a radioactive calibration phantom comprising a radioactive material to acquire scan data, and a gamma counter that measures a radioactivity level of a sample of the radioactive material to acquire measurement data. The system further includes a processor that executes computer-executable instructions stored in a memory, the instructions including generating one or more cross-calibration factors from the scan data and the measurement data.

In accordance with another aspect, a method of optimizing an plasma input function for a patient under study includes scanning a radioactive calibration phantom comprising a radioactive material to acquire nuclear scan data, measuring a radioactivity level of a sample of the radioactive material to acquire measurement data, and generating one or more cross-calibration factors from the scan data and the measurement data.

In accordance with another aspect, a method of optimizing a plasma input function for a patient under study includes acquiring positron emission tomography (PET) scan data of a patient in list mode, reconstructing the acquired PET scan data into a nuclear image, and identifying arterial regions in the nuclear image. The method further includes assessing a sampling window for sampling early bolus activity in the acquired PET scan data to determine whether the sampling window provides a predetermined level of accuracy for generating an initial time-activity curve (TAC), adjusting the sampling window when the sampling window does not provide the predetermined level of accuracy, and reconstructing additional nuclear images when the sampling window provides the predetermined level of accuracy. Additionally, the method includes generating the initial TAC, collecting venous samples from a patient during PET scan data acquisition after infusing the patient with a radioactive tracer, measuring the venous samples in a gamma counter, and comparing radioactivity levels measured in the gamma counter to levels indicated in the TAC. Furthermore, the method includes adjusting the TAC until activity levels in the TAC coincide with activity levels measured in the gamma counter, generating an arterialized input function (AIF) as a function of the adjusted TAC, and outputting the AIF to at least one of a display for presentation to a user and a memory for storage.

One advantage is that input function estimation is improved.

Another advantage resides in minimizing invasiveness of the blood sampling procedure.

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

The subject innovation overcomes the aforementioned problems in the art by acquiring scan data in list-mode and retrospectively binning the data to generate an image that includes the arterial region. When data is collected in the list mode, the raw data is stored in a list with each entry carrying a time stamp denoting the time of acquisition. This keeps the raw data available for later analysis or reuse (e.g. re-reconstructed) even after the diagnostic image has been reconstructed. Because the data is collected and stored in list-mode, the size of the temporal bin can be retrospectively adjusted and the process repeated for different size or temporarily shifted bins until the true peak is determined. During the imaging process, as blood samples are drawn and the concentration of the tracer in the samples is measured empirically. Because these samples are drawn relatively late in the imaging process, the concentration of the radiopharmaceutical in the arteries and the blood vessels has substantially equalized. The plurality of samples taken at known times are used to scale or adjust a curve of arterial blood concentration versus time in order to calibrate the true arterial input function.

The herein-described systems and methods provide a streamlined, integrated work-flow for generating arterialized image-derived input functions for kinetic analysis of novel tracers. The entire sequence of acquisition (dynamic image acquisition, venous blood sampling, etc.) and processing steps such as optimized reconstruction protocol, contouring arterial regions in the image, correcting the image derived input function for sub-optimal temporal sampling, as well as partial volume and spillover effects, are all implemented on the same platform, greatly simplifying the procedure.

Figure 1:
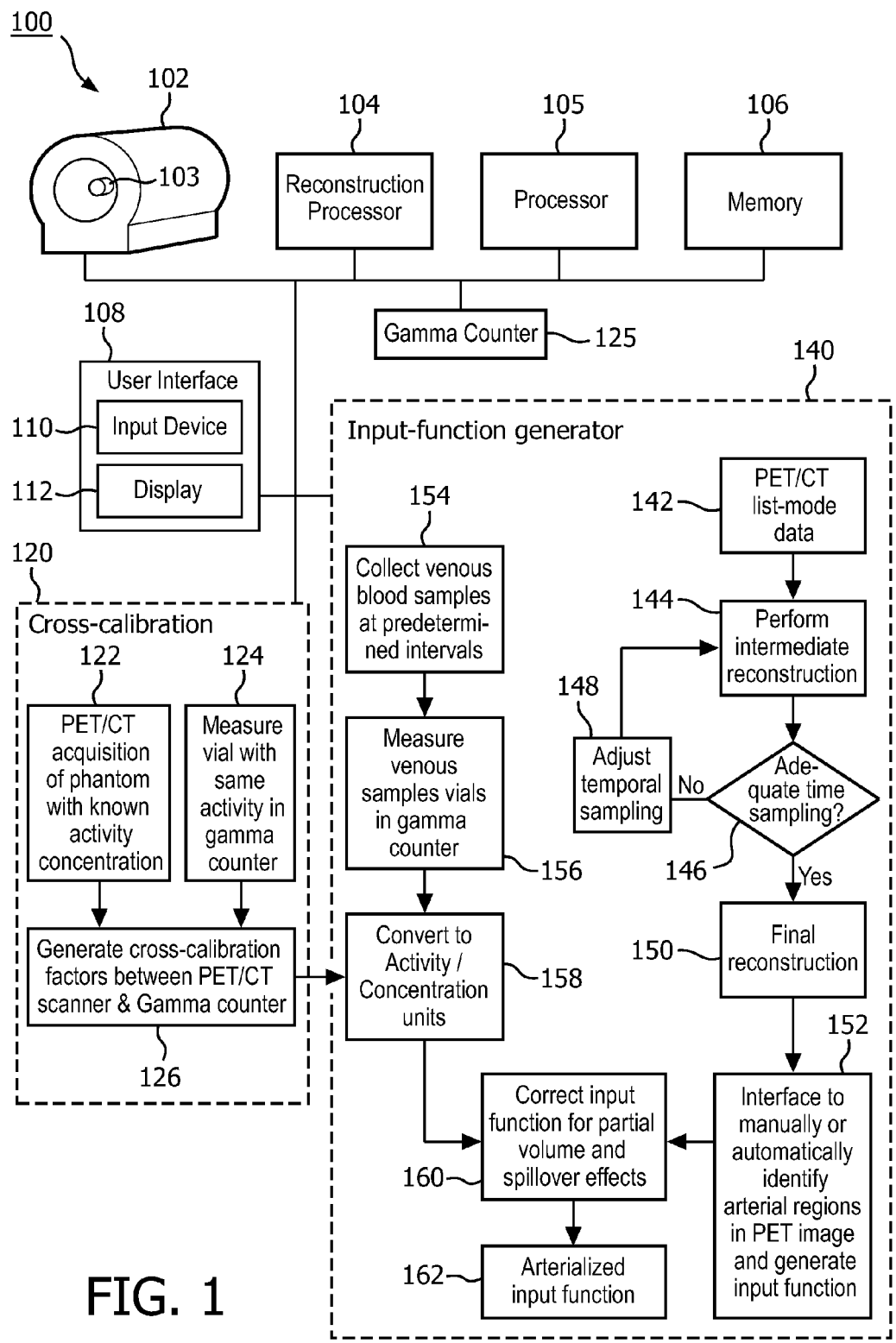
FIG. 1 illustrates a system for generating arterialized image-derived input functions used in kinetic analysis and therapy efficacy evaluation, in accordance with one or more aspects described herein.

FIG. 1 illustrates a system 100 for generating arterialized image-derived input functions used in kinetic analysis and therapy efficacy evaluation, in accordance with one or more aspects described herein. Accurate determination of changes in physiological parameters during or at the completion of therapy is important in personalized therapy in order to determine the effectiveness of treatment. For example, PET dynamic imaging incorporating pharmacokinetic modeling can provide absolute quantification measures of metabolism, perfusion, and proliferation among others. Monitoring changes in these parameters during the course of therapy can provide a measure of treatment response, whereby ineffective therapies can be adapted or discontinued early on and alternative treatments can be offered. The successful incorporation of these imaging biomarkers for predicting treatment response strongly depends on their accuracy and reproducibility. The accuracy of these quantitative measurements depends on the quality of the measured plasma input function. The described innovation provides streamlined, integrated systems and methods for generating arterialized image-derived input functions used in kinetic analysis.

The system 100 includes a nuclear medicine scanner (e.g., PET or SPECT) 102, which scans a phantom 103 to acquire raw emission data that is used to calibrate the scanner. The nuclear medicine scanner is also used to scan a subject or patient to scan raw data of the subject or patient. A reconstruction processor 104 reconstructs the raw data into an emission image of one or more anatomical structures (i.e., a volume of interest) in the patient. The system further includes a processor 105 that executes, and a memory 106 that stores, computer-executable instructions for performing the various acts, functions, methods techniques, procedures, etc., described herein. The memory 106 also stores the list mode data. Additionally, the system 100 includes a user interface 108 that comprises a user input device 110 (e.g., a keyboard, microphone, stylus, mouse, touch pad, touch screen, etc.) by which a user enters information into the system, and a display 112 on which information is presented to the user.

As is known in the art, when an electron and positron meet, they annihilate, emitting two 511 keV gamma rays that are oppositely directed in accordance with the principle of conservation of momentum. In PET data acquisition, two substantially simultaneous or coincident 511 keV gamma ray detection events are presumed to have originated from the same positron-electron annihilation event, which is therefore located somewhere along the "line of response" (LOR) connecting the two substantially simultaneous 511 keV gamma ray detection events. This line of response is also sometimes called a projection, and the collected PET data is referred to as projection data.

In conventional PET, two 511 keV gamma ray detection events occurring within a selected short time or coincidence window, such as within 6 nanoseconds of each other, are taken as defining a valid LOR. Due to the variable annihilation position with respect to the detector elements a small (e.g., sub-nanosecond) time difference between the coincident gamma photon detection events occurs. A related technique, called time-of-flight PET or TOF-PET, takes advantage of this small time difference to further localize the positron-electron annihilation event along the LOR. In general, the annihilation event occurred along the LOR at a point closer to the gamma ray detection event that occurred first. If the two gamma ray detection events occur simultaneously within the time resolution of the detectors, then the annihilation event occurred at the midpoint of the LOR. The two detection events that define each LOR are stored, with their respective time stamps, in the memory 106 in the list-mode.

As stated above, the system 100 includes the processor 105 that executes, and the memory 106, which stores, computer-executable instructions (e.g., routines, programs, algorithms, software code, etc.) for performing the various functions, methods, procedures, etc., described herein. Additionally, "module," as used herein, denotes a set of computer-executable instructions, software code, program, routine, or the like, as will be understood by those of skill in the art.

The memory may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor can read and execute. In this context, the systems described herein may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

The system 100 further includes a cross-calibration module or processor 120, which executes an algorithm or workflow for cross-calibrating the nuclear scanner 102. For instance, when the nuclear scanner is a multi-modal scanner that acquires both PET and computed tomography (CT) data, then at 122, PET/CT data acquisition is performed by scanning a radioactive phantom with a known radioactivity concentration. At 124, a sample vial with a radioactivity level that is the same as that of the phantom is measured in a gamma counter 125. At 126, cross-calibration factors are generated from the acquired PET/CT data and the measurement data provided by the gamma counter.

The system 100 also includes an input function generator or processor 140 that executes an algorithm or workflow for optimizing an input function, in accordance with various aspects described herein. For instance, at 142, the scanner 102 is controlled to acquire PET/CT data by scanning a patient and storing the acquired data in list mode. At 144, an intermediate reconstruction is performed to generate an intermediate image of the patient. At 146, a determination is made regarding whether a sampling rate or window for sampling early bolus activity is sufficient to provide a desired predetermined level of accuracy for generating an initial input function. If not, then the sampling rate or window is adjusted by looking at the time stamps to select a different length for time shifted sampling windows, at 148. The workflow reverts at 146 to reconstruct the re-binned list mode data is used to generate another intermediate reconstructed image but with a different, e.g. shorter, sampling window than the first intermediate image. When the sampling rate or window is satisfactory (i.e., when a user is satisfied with the accuracy of the intermediate reconstructed image), a final reconstruction of the PET image is generated, at 150. At 152, arterial regions in the final PET image are manually or automatically identified and the system generates an initial input function. The user interface 108 is used to manually identify the arterial region(s) or for a user to verify on automatic identification.

At 154, venous samples are collected from the patient during the PET scan at predetermined intervals, typically sufficiently late in the study that concentrations in the arteries and veins have equilibrated. At 156, vials containing the venous samples are measured in the gamma counter 125. At 158, measured venous sample measurement data collected at 156 is converted to activity/concentration units using the cross-calibration factor(s) generated at 126 by the cross-calibration module 120. At 160, the initial input function is adjusted to correct for partial volume and spillover effects. At 162, an arterialized (final) input function is output. The arterialized input function, as well as any other data generated by the system 100 and/or components thereof is stored in the memory 106 and can be recalled or accessed by the user for viewing on the display 112.

With regard to the effect of scanner resolution on image-derived input functions, partial volume effects due to limited scanner resolution and spillover of activity from nearby structures can affect the overall shape of the input function. A number of investigators have looked into this problem and shown that by calibrating the image-derived input function against a few late-time venous blood samples (typically 3 samples), the estimated initial input function can be "arterialized". See, e.g., Chen, K., et al., *Characterization of the image-derived carotid artery input function using independent component analysis for the quantitation of [18F] fluorodeoxyglucose positron emission tomography images*. Phys Med Biol, 2007. 52(23): p. 7055-71. See also, e.g., Hoekstra, C. J., O. S. Hoekstra, and A. A. Lammertsma, *On the use of image-derived input functions in oncological fluorine-18 fluorodeoxyglucose positron emission tomography studies*. Eur J Nucl Med, 1999. 26(11): p. 1489-92. These have shown that the addition of a few venous blood samples provides similar results to an arterial sampled input function. Moreover, collecting 3 venous blood samples (1 ml in volume) late in the dynamic acquisition is less invasive and safer for the patients than a protocol which involves arterial sampling.

Accordingly, in one embodiment, the system 100 is employed to perform quality control and calibration for image derived input functions. For instance, several (e.g., three) venous blood samples can be collected, each approximately 1 ml in volume, towards the end of the dynamic acquisition scan. Radioactivity in the vials is counted using the gamma counter 125, such as a Packard Cobra™ Gamma Counter. The cross-calibration factor is applied between the gamma counter and PET scanner to convert venous sample activity to concentration units (Bq/cc). Finally, partial volume and spillover corrections are applied to image-derived input function using the venous blood samples. In this manner, the system 100 provides a systematic framework that improves the quality of input function estimation resulting in reliable and accurate measurement of physiological parameters, subsequently enabling accurate prediction of treatment response in patients.

Figure 2:
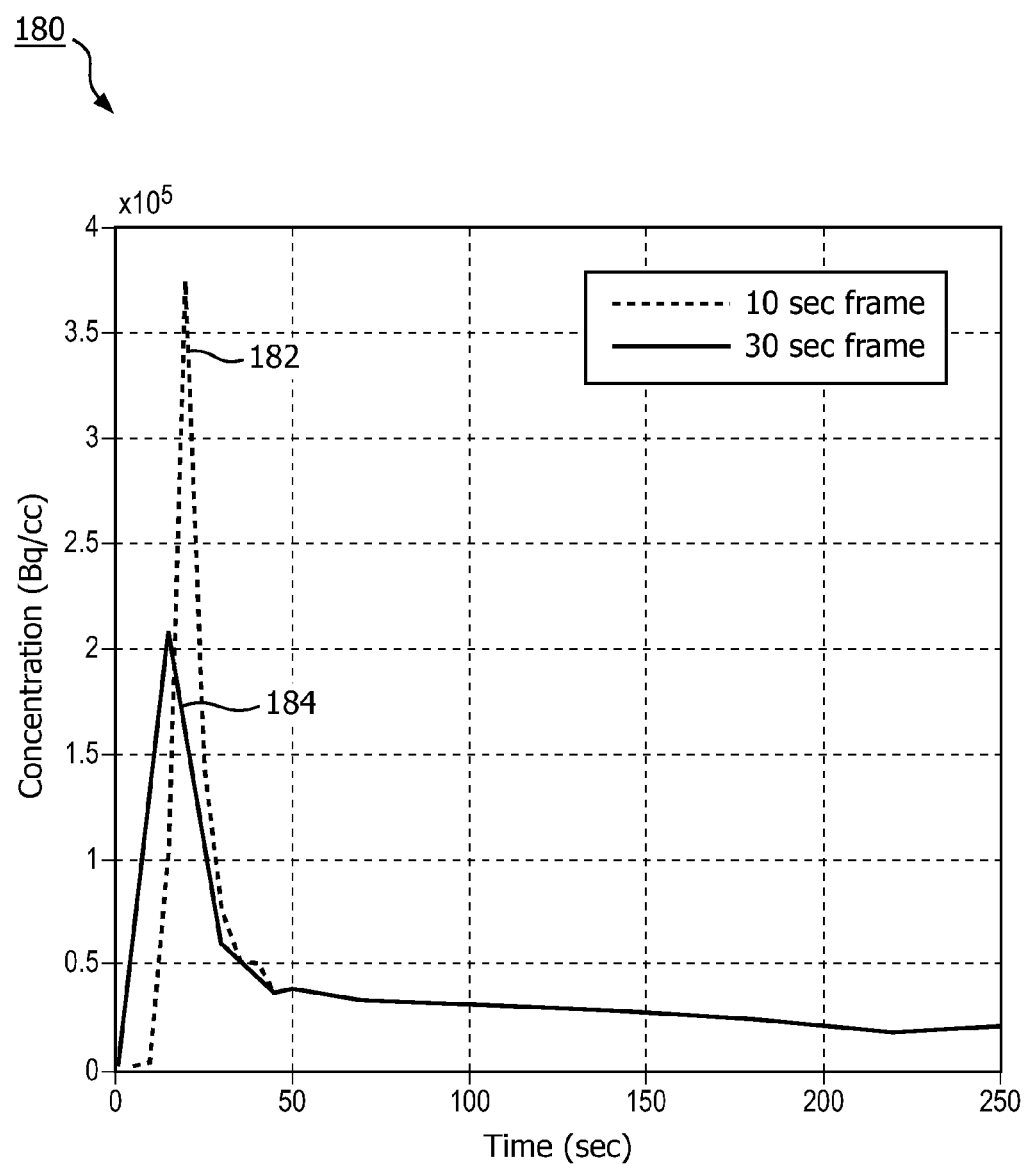
FIG. 2 illustrates optimal and sub-optimal temporal sampling of an image derived input function.

FIG. 2 illustrates optimal and sub-optimal temporal sampling of an image derived input function. When the early activity (e.g., less than 50 seconds) for the TAC 182 is sampled every 10 seconds, it exhibits an impulse-like shape. When the same data is initially sampled only every 30 seconds, such as is the case for the TAC 184, a significant reduction in the magnitude of the peak as well a peak shift in time is observed. Coarse temporal sampling thus reduces the magnitude (height) of the input function peak, which can result in an incorrect kinetic model estimates (e.g., FDG influx rate, cerebral blood flow). In older generation PET scanners, the temporal sampling scheme for dynamic studies was fixed prior to acquisition with no recourse to changing the sampling scheme once the acquisition was complete. This was mainly due to the fact that raw data was binned and stored as 4D sinograms due to storage and memory considerations. However, current generation scanners such as the GEMINI™ TF PET/CT scanners from Philips Medical Systems store the data in list mode, making it possible to change the temporal sampling, especially early in the course of tracer distribution through the arterial and venous systems.

When using a long sampling window (e.g., 30 seconds), there is ample data in for reconstruction in each window, but the count rate is averaged over a longer period, and therefore magnitude of the TAC may be reduced. When using a short sampling window (e.g., 10 seconds), high temporal resolution of the count rate is achieved, but a scarcity of data in each window can cause artifacts to degrade the reconstructed image. Accordingly, the described systems and methods relate to adjusting sampling window settings to optimize the TAC curve. In this manner, an optimized sampling window can be identified, which is sufficiently long to permit a satisfactory image quality and sufficiently short to achieve high temporal resolution of the count rate. In one embodiment, approximately three venous samples are used, along with the artery volume image values at the same times, to scale the amplitude of the TAC.

Figure 3:
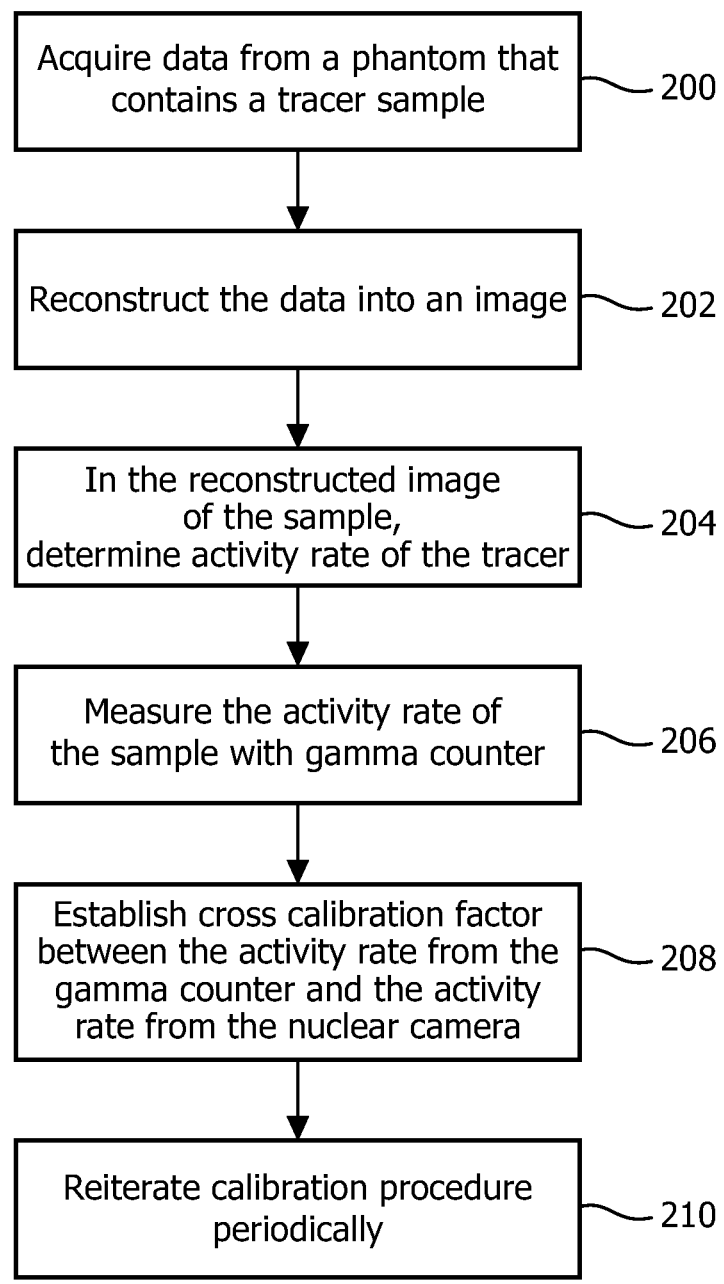
FIG. 3 illustrates a method for generating cross-calibration factors that facilitate calibrating a nuclear scanner, such as a PET or SPECT scanner, in accordance with one or more aspects described herein.
Figure 4:
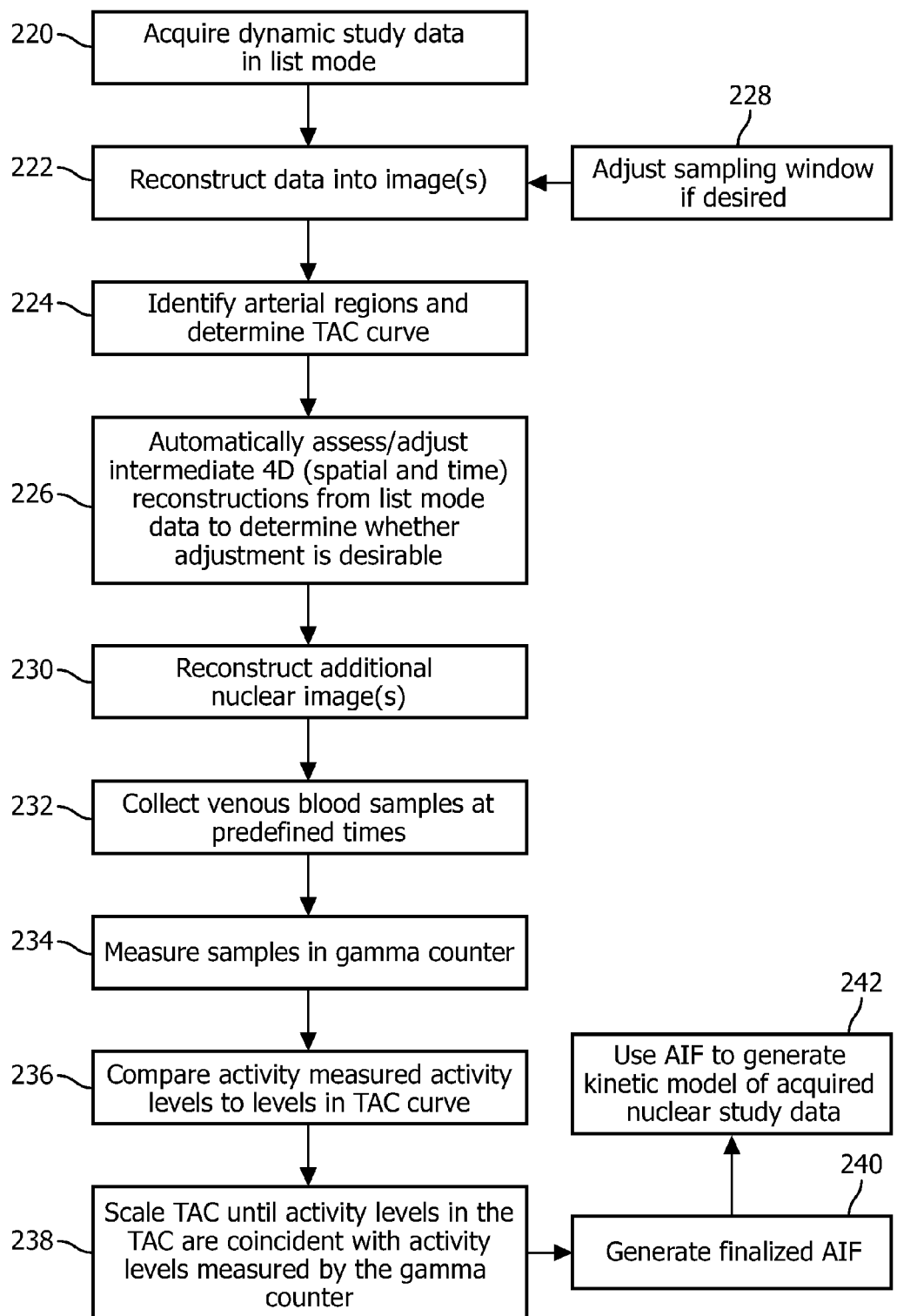
FIG. 4 illustrates a method of refining an input function used for kinetic modeling of dynamically acquired PET data, in accordance with one or more aspects described herein.

FIGS. 3 and 4 illustrate a methods related to refining an input function used for kinetic modeling of acquired PET data, in accordance with various features. While the methods herein are described as a series of acts, it will be understood that not all acts may be required to achieve the described goals and/or outcomes, and that some acts may, in accordance with certain aspects, be performed in an order different that the specific orders described.

FIG. 3 illustrates a method for generating cross-calibration factors that facilitate calibrating a nuclear medicine scanner, such as a PET or SPECT scanner, in accordance with one or more aspects described herein. At 200, emission data is acquired from a phantom that contains a sample, e.g. vial of the tracer. In one embodiment, the tracer is an 18F (fludeoxyglucose-18) tracer. An emission image is reconstructed from the acquired emission data and a subvolume of the image corresponding to the sample vial is identified, at 202. At 204, an image value indicative of the activity level in the subvolume corresponding to the sample vial is determined. At 206, the activity level of the sample in the vial is measured in the gamma counter 125. At 208, a cross-calibration factor is determined between the activity levels as measured by the gamma counter 125 and PET/CT scanner image values. At 210, the procedure is optionally iterated on a periodic basis (e.g., monthly, quarterly, etc.) to verify the cross-calibration factor.

FIG. 4 illustrates a method of refining an input function used for kinetic modeling of dynamically acquired PET data, in accordance with one or more aspects described herein. At 220, PET data is acquired in list-mode format. At 222, the data is reconstructed with a nominal sampling/binning window to generate a series of images at short terminal intervals. At 224, the time and activity curve (TAC) of FIG. 2 is determined for the early bolus activity in the arterial volume. At 226, the sampling/binning window width is adjusted, e.g. shortened, and the reconstruction is repeated. In one embodiment, the temporal width of the sampling in the initial 60-120 seconds is chosen such that a predefined noise-level is not exceeded. Based on decay statistics, this may lead to a sampling window of e.g. 10 s, although other sampling window widths or ranges thereof are contemplated (e.g., 5 s, 15 s, 20 s, etc.). The sampling window is iteratively adjusted at 228 until the early bolus activity exhibits a sharp peak or is otherwise optimized. Additional images, e.g. a series of diagnostic images, are generated at 230 over the course of the emission study, typically with a sampling window dictated by the nuclear imaging protocol. The arterial volume continues to be monitored and the TAC is adjusted and/or plotted at 224.

At 232, venous blood samples are collected at known time points, sufficiently long into the nuclear imaging study that the activity in arterial and venous blood as equalized. At 234 the activity level in blood samples is measured with the gamma counter 125. In one embodiment, the user interface 108 (FIG. 1) prompts a technician or user to collect venous samples at specific times, count activity of blood samples in the gamma counter 125. At 236 the activity level as measured from the TAC curve at the time the blood samples were taken are compared with the activity levels measured by the gamma counter 125. At 238, the TAC is scaled to bring the activity levels of the TAC into coincidence with the activity levels measured by the gamma counter. At 240, the finalized arterial input function (AIF) is generated and at 242 the AIF is used for kinetic modeling of the acquired dynamic nuclear study data.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A system that facilitates cross-calibrating a nuclear scanner to a gamma counter, including:
   a nuclear scanner configured to scan:
      a radioactive calibration phantom comprising a radioactive material to acquire scan data; and
      a patient to acquire list mode data;
   a gamma counter that measures a radioactivity level of a sample of the radioactive material to acquire measurement data; and
   a processor that executes computer-executable instructions stored in a memory, the instructions including:
      generating one or more cross-calibration factors from the scan data and the measurement data;
      generating a reconstructed series of nuclear images by reconstructing the list mode data in each of a series of temporal sampling windows;
      generating an initial time-activity curve (TAC) based on nuclear image data; and
      determining a sampling window in which early bolus activity in the TAC provides a predetermined level of accuracy.

2. The system according to claim 1, wherein the instructions further include:
   identifying arterial regions in the nuclear images; and
   generating the initial time-activity curve (TAC) based on nuclear image data in the identified arterial regions.

3. The system according to claim 2, wherein the instructions further include:
   iteratively adjusting the sampling window and reconstructing the series of images.

4. The system according to claim 2, wherein the instructions further include:
   measuring venous samples in the gamma counter, the venous samples being collected from the patient at determined intervals during the patient scan data acquisition; and
   converting radioactivity level information in the venous samples to concentration values.

5. The system according to claim 4, wherein the instructions further include:
   correcting the initial TAC using the radioactivity level information from the venous samples; and
   outputting an arterialized input function to at least one of a display for presentation to a user and a memory for storage or usage in pharmacokinetic studies.

6. The system according to claim 2, wherein the nuclear scanner is a multi-modal positron emission tomography (PET)/computed tomography (CT) scanner and the acquired patient scan data includes PET scan data and CT scan data.

7. The system according to claim 2, wherein an initial width of the sampling window is in the range of 5 to 15 seconds.

8. The system according to claim 2, wherein venous samples are collected from the patient during a nuclear scan and approximately 1-2 minutes after infusing the patient with a radioactive tracer.

9. The system according to claim 1, wherein the radioactive material includes fluorodeoxyglucose 18 (18F).

10. A method of optimizing a plasma input function for a patient under study, including:
  scanning a radioactive calibration phantom comprising a radioactive material to acquire nuclear scan data;
  measuring a radioactivity level of a sample of the radioactive material to acquire measurement data; and
  generating one or more cross-calibration factors from the scan data and the measurement data;
  generating an initial time-activity curve (TAC) based on nuclear image data; and
  determining a sampling window in which early bolus activity in the TAC provides a predetermined level of accuracy.

11. The method according to claim 10, further including:
  acquiring patient scan data of a patient in list mode;
  generating a series of nuclear images by reconstructing the list mode data in each of a series of temporal sampling windows;
  identifying arterial regions in the nuclear images; and
  generating the initial time-activity curve (TAC) based on nuclear image data in the identified arterial regions.

12. The method according to claim 11, further including:
  iteratively adjusting the sampling window and reconstructing the series of images.

13. The method according to claim 11, further including:
  measuring venous samples in a gamma counter, the venous samples being collected from the patient at determined intervals during the patient scan data acquisition;
  converting radioactivity level information in the venous samples to concentration values.

14. The method according to claim 13, further including:
  correcting the initial TAC using the radioactivity level information from the venous samples; and
  outputting an arterialized input function to at least one of a display for presentation to a user and a memory for storage or usage in pharmacokinetic studies.

15. The method according to claim 11, wherein the patient scan data is acquired by a multi-modal positron emission tomography (PET)/computed tomography (CT) scanner and the acquired patient scan data includes PET scan data and CT scan data.

16. The method according to claim 11, wherein an initial width of the sampling window is in the range of 5 to 15 seconds, and wherein venous samples are collected from the patient during a nuclear scan and approximately 1-2 minutes after infusing the patient with a radioactive tracer.

17. The method according to claim 10, wherein the radioactive material includes fluorodeoxyglucose 18 (18F).

18. A processor or non-transitory computer-readable medium carrying a computer program that controls one or more processors configured to:
  scan a radioactive calibration phantom comprising a radioactive material to acquire nuclear scan data;
  measure a radioactivity level of a sample of the radioactive material to acquire measurement data; and
  generate one or more cross-calibration factors from the scan data and the measurement data;
  generate an initial time-activity curve (TAC) based on nuclear image data; and
  determine a sampling window in which early bolus activity in the TAC provides a predetermined level of accuracy.

19. A method of optimizing a plasma input function for a patient under study, including:
  acquiring positron emission tomography (PET) scan data of a patient in list mode;
  reconstructing the acquired PET scan data into a nuclear image;
  identifying arterial regions in the nuclear image;
  assessing a sampling window for sampling early bolus activity in the acquired PET scan data to determine whether the sampling window provides a predetermined level of accuracy for generating an initial time-activity curve (TAC);
  adjusting the sampling window when the sampling window does not provide the predetermined level of accuracy;
  reconstructing additional nuclear images when the sampling window provides the predetermined level of accuracy;
  generating the initial TAC;
  collecting venous samples from a patient during PET scan data acquisition after infusing the patient with a radioactive tracer;
  measuring the venous samples in a gamma counter;
  comparing radioactivity levels measured in the gamma counter to levels indicated in the TAC;
  adjusting the TAC until activity levels in the TAC coincide with activity levels measured in the gamma counter;
  generating an arterialized input function (AIF) as a function of the adjusted TAC; and
  outputting the AIF to at least one of a display for presentation to a user and a memory for storage.

* * * * *